United States Patent [19]

Klose et al.

[11] Patent Number: 4,898,832
[45] Date of Patent: Feb. 6, 1990

[54] PROCESS FOR CARRYING OUT ANALYTICAL DETERMINATIONS AND MEANS FOR CARRYING OUT THIS PROCESS

[75] Inventors: Sigmar Klose, Berg; Fritz Stähler, Tutzing, both of Fed. Rep. of Germany

[73] Assignee: Boehringer Mannheim GmbH, Mannheim, Fed. Rep. of Germany

[21] Appl. No.: 147,610

[22] Filed: Jan. 25, 1988

Related U.S. Application Data

[63] Continuation of Ser. No. 413,012, Aug. 30, 1982, abandoned.

[30] Foreign Application Priority Data

Sep. 1, 1981 [DE] Fed. Rep. of Germany ....... 3134611

[51] Int. Cl.$^4$ ............................................. G01N 21/07
[52] U.S. Cl. ...................................... 436/45; 422/72; 356/427
[58] Field of Search ................ 422/72, 61, 102, 100, 422/104; 436/45; 356/244, 246, 426, 427

[56] References Cited

U.S. PATENT DOCUMENTS

| | | | |
|---|---|---|---|
| 3,532,470 | 10/1970 | Rochte | 422/61 |
| 3,795,451 | 3/1974 | Mailen | 422/72 |
| 3,972,595 | 8/1976 | Romankui et al. | 350/267 |
| 4,042,335 | 8/1977 | Clément | 422/56 |
| 4,237,234 | 12/1980 | Meunier | 422/72 |
| 4,277,561 | 7/1981 | Monget et al. | 422/56 |
| 4,279,862 | 7/1981 | Bretaudiere et al. | 422/72 |
| 4,314,968 | 2/1982 | Guigan | 436/45 |
| 4,387,164 | 6/1983 | Hevey et al. | 422/72 |
| 4,390,499 | 6/1983 | Curtis et al. | 422/61 |
| 4,426,451 | 1/1984 | Columbus | 422/102 |
| 4,431,606 | 2/1984 | Revillet et al. | 422/102 |

FOREIGN PATENT DOCUMENTS

| 52769 | 6/1982 | European Pat. Off. | 422/72 |
|---|---|---|---|
| 52770 | 6/1982 | European Pat. Off. | 422/72 |

Primary Examiner—Michael S. Marcus
Attorney, Agent, or Firm—Felfe & Lynch

[57] ABSTRACT

A process for carrying out an analytical determination by mixing and incubating a sample solution with at least one reagent and measuring a parameter in the reaction mixture, the sample solution being transported from an application point to a measurement point, wherein a sample solution is first transported to a soluble dry reagent, with at least partial dissolving of the latter, and then further transported to a measurement point, the transport taking place by two different forces, whereby, at least on a part of the transport path, it is brought about by a surface force acting on the solution as a first force, which, for the regulation of the transport velocity or transport direction, is superimposed by a centrifugal force and/or pressure force as a second force which, depending upon which transport state of the fluid is to be adjusted, is made greater or smaller than the first force.

5 Claims, 8 Drawing Sheets

PROCESS FOR CARRYING OUT ANALYTICAL DETERMINATIONS AND MEANS FOR CARRYING OUT THIS PROCESS

This application is a continuatin, of application Ser. No. 413,012, filed Aug. 30, 1982, now abandoned.

This invention relates to a process for carrying out analytical determinations and with apparatus therefor. More specifically, the inventive method and apparatus involves mixing and incubating a sample solution with at least one reagent and measuring a parameter in the reaction mixture.

The use of dry reagents on appropriate inert carrier materials has long been known for carrying out chemical reactions which can be used for the qualitative or quantitative detection of a substance to be analysed. As examples, there may be mentioned Federal Republic of Germany patent specifications Nos. 23 32 760; 27 17 817; 27 52 352 and 29 27 345 and European patent specification No. 0014 797. A common feature of these processes is that a sample present as a solution is applied to the reagent carrier. From the point of application, the sample then diffuses into the carrier due to the action of capillary forces.

On the way, reagents are wholly or partly dissolved and the reagent-sample solution thus formed passes on further until finally it reaches a measurement zone where the change of colour intensity is measured optically. In each case, the measurement zone is an integral component of the reagent carrier.

As is to be understood, for example, from Federal Republic of Germany patent specification No. 29 27 345, processes in which the diffusion process proceed uncontrolled and in which the remission of light beams directly on the reagent carrier, which generally consists of an opaque layer, is measured, give rise to considerable problems. Fibre materials show non-uniformities which, in the micro range, lead to differering rates of spreading out of the liquids and zones result with reagent concentrations which are higher or lower than the optimum. Thus, for example, in European patent specification No. 0014 797, it is mentioned that air pockets in the carrier materials lead to additional difficulties and the conclusion is drawn that fluid currents which are produced by capillary forces must be "controlled".

A second important disadvantage concerns the remission measurement itself: in contradistinction to transmission photometry, in this case there is no linear relationship between the concentration of a light-absorbing substance and the extinction. More or less strongly curved calibration curves are obtained upon which the surface properties have a strong influence. In this is to be seen a fundamental disadvantage which has a strong negative influence on the reproducibility of an analytical evaluation process. Furthermore, tests which depend upon the measurement of forming or decreasing turbidities (turbidimetric processes) can, in principle, not be carried out therewith. However, in the case of immunological methods and also in the case of enzyme determinations, such as the lipase determination, these represent a widely-used and dependable technique.

A further disadvantage of such analysis elements is that differing reaction phases in the case of multi-step reactions on separate layers of the analysis element cannot be controlled in a definite manner. This means that the starting points of subsequent reactions depend upon the non-constant diffusion rate of the solution.

Also in the laminar arrangement itself, a disadvantage is to be seen since the contact surfaces of reagents, which, with regard to their stability, can be unfavourably influenced, are relatively large. It would be more favourable to arrange such reagents in a reagent carrier strictly separated from one another.

From the above, it follows that, in the sense of the achievement of analysis results with maximum correctness and reproducibility, it is necessary to avoid the mentioned disadvantages since they place relatively narrow limits on the field of use of such analysis elements which are constructed from reagent carriers.

From the point of view of the user, such techniques for carrying out tests are advantageous insofar as they permit a very simple handling, since no reagent solutions have to be used, the pipetting of reagents is avoided and no stability problems arise with the reagents which are always more unstable in solution and the like.

It is an object of the present invention to retain these advantages and, at the same time, to overcome the described disadvantages.

Thus, according to the present invention, there is provided a process for carrying out an analytical determination by mixing and incubating a liquid sample with at least one dry reagent which at least partially dissolves into the sample and measuring a parameter in the reaction mixture thereof, the sample and reaction mixture being transported along a path from a sample application point to a reaction-mixture measurement point, passing through, in part, a zone with the soluble dry reagent for the at least partial dissolving of the latter, and then further transported to the measurement point, the transport taking place by two different forces, one of which is a surface force between the transport path and the one of the liquid sample and reaction mixture therein and at least one of which is controllably variable for the regulation of the transport velocity or transport direction, for example a centrifugal force and/or pressure force as a second force which, depending upon which transport state of the fluid is to be adjusted, is made greater, equal to or smaller than the first force.

This new process combines the advantages of the described reagent carrier technique with the exactitude and freedom from error of conventional wet chemical processes.

This is achieved in that the sample solution to be analysed (generally diluted with water) is applied at an introduction point from whence, on the way to a measurement point, it flows through one or more carriers of dry reagents, the reagents thereby being wholly or partly dissolved. The flowthrough takes place with strict control of the flow velocity and thus of the flow times, in that the driving surface force is superimposed by a second force which accelerates, impedes or stops the flow. At the end of the flow path, the fluid then reaches a measurement point, which is not identical with the reagent carrier, in which a reaction signal, preferably the optical transmission, is measured.

As reagents, on the one hand there thereby come into question those which can be wholly or partly dissolved off from the carrier material, for example buffer substances, salts and enzymes or their substrates, and on the other hand, those which are adsorbtively or convalently bound to the carrier material and on which a solid phase reaction can then take place, for example, ion exchangers and carrier-bound biologically-active substances, such as enzymes, antibodies, antigens or the like.

For the measurement of a reaction signal, there can be used, for example, apart from the already mentioned optical transmission, depending upon the embodimental form of the measurement point, also electrode potentials, electrical conductivity, fluorescent radiation or the like.

In the following, the present invention is described in more detail, with reference to the accompanying drawings, in which.

Depending upon the superimposed forces ($K_2$), there are essentially two embodiments of the present invention, the driving forces ($K_1$) being, in each case, surface or capillary forces.

In the case of the first embodiment, $K_2$ is a centrifugal force.

In the case of this analysis system, exchangeable insert elements for centrifugal analysis rotors, which consist, for example, of a plastics formed body of polystyrene, Plexiglass, polyurethane or the like, as well as reagent carrier zones, which consist of an absorbent carrier material which is impregnated with the reagent, or other small reagent-filled hollow spaces, for example a surface structure in the plastics body, which are placed in the plastics body, and a closure foil are placed on a rotor of a centrifuge in such a manner that the fluid-moving capillary force can be controlled by the centrifugal force. For this purpose, it is necessary that different speeds of rotation and thus different centrifugal forces can be adjusted.

Figure 1A:
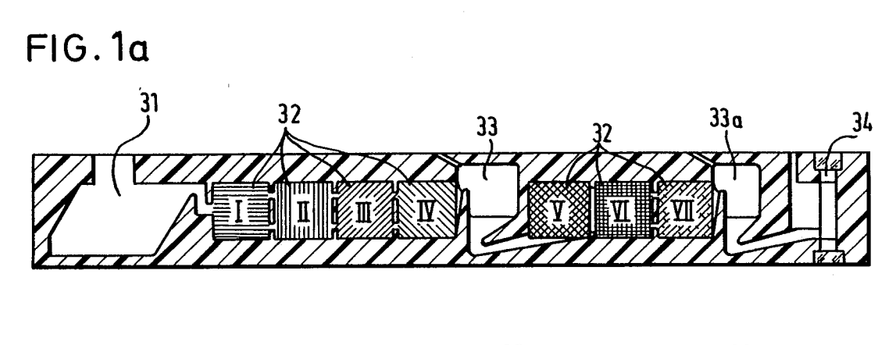
FIGS. 1a and 1b show upper and side views of an insert element appropriate for the present invention.
Figure 1B:
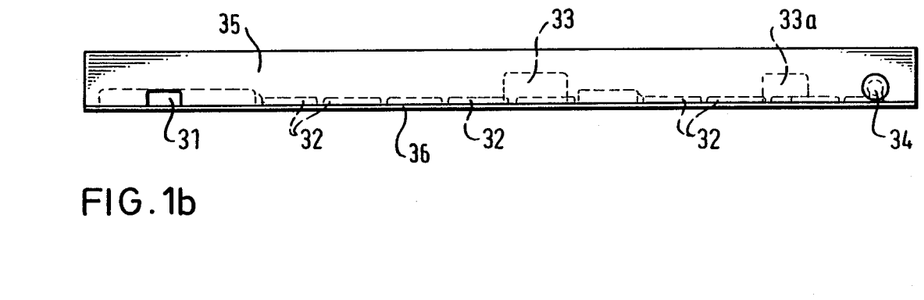

The course of the analysis in the case of this embodiment of the present invention is dscribed in more detail with reference to FIGS. 1a and 1b of the accompanying drawings, FIG. 1a showing a plan view of an insert element suitable for the present invention and FIG. 1b a sectional side view.

Figure 2:
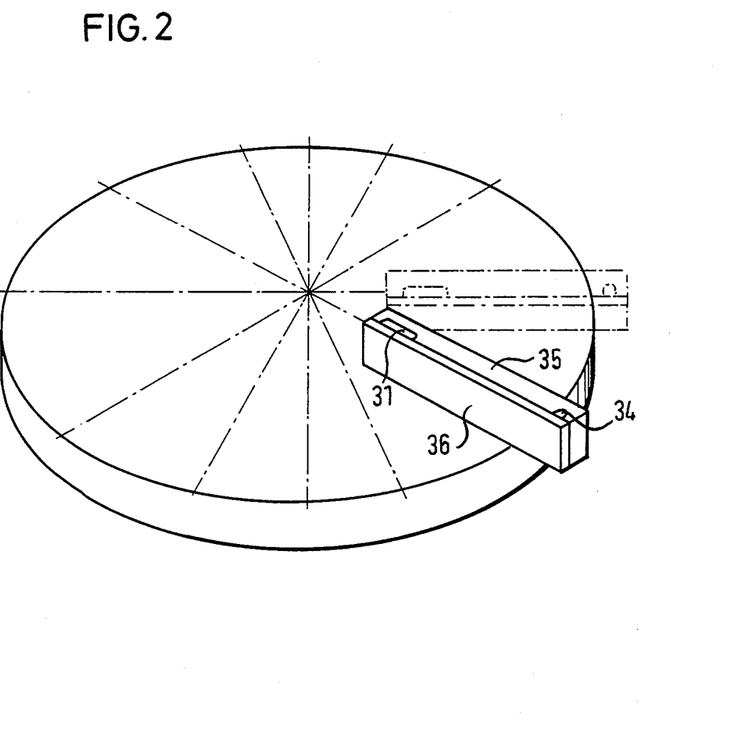
FIG. 2 is an illustration of the element of FIGS. 1a and 1b on a rotor.

FIG. 2 schematically illustrates how the insert element of FIG. 1 is applied to an appropriate centrifuge rotor, such as is described, for example, in Federal Republic of Germany patent specification No. 30 44 372, (=U.S. patent application Ser. No. 323,343 filed Nov. 20, 1981) by holding means which are not illustrated.

As is shown in FIG. 1a, in a plastics formed body there is provided a sample application chamber (31) which is connected with various reagent zones I to VII. Each reageant zone consits of a piece of absorbent carrier impregnated with a particular reagent, for example paper or fleece. (33) and (33a) are mixing valves I and II and (34) indicates the measurement point (cuvette). FIG. 1b shows the insert element of FIG. 1a in side view. (35) indicates the plastics base body and (36) the closure foil by means of which the sample application chamber, the reagent zone mixing valves and the measurement point are covered.

The carrying out of the process of the present invention wil now be described in more detail, with reference to FIGS. 1 and 2.

A sample is introduced into the sample application chamber (31). A particular speed of rotation U1 is then adjusted which is suitable for passing the sample to the reagent zone I (32). As soon as contact is established, the capillary force sucks up the solution, i.e. the solution is transported over the reagent zone (32). If the centrifugal force Z1 is smaller than the capillary force K1, the solution remains in the zone (32). If the centrifugal force Z1 is smaller than the capillary force K1, the solution remains in the zones (32) insofar as the take up volume of the zone is greater than the volume of the applied sample. Thus, with the condition $Z1 < K1$, the residence or incubating time of the solution in RI is precisely fixed. If the centrifugal force is now increased to Z2 so that $Z2 > K1$, the solution enriched by the reagent present on R I leaves this zone and comes into contact with reagent zone R II. The procedure is here repeated. The solution is distributed over R II, i.e. is further transported. The above-described conditions here apply analogously.

The procedure can be repeated as often as desired and, in the case here described, reagent zones I to IV are passed through. The insert elements can naturally be constructed in a different manner and have also more or less reagent zones. The forces $K_n$ and $Z_n$ are practically freely selectable, which, especially for the latter, can be accomplished very simply by the smooth adjustment of Z. The carrying out of the analysis process thereby achieves the advantage that the time necessary therefor can be kept as short as possible. Therefore, the residence time of the solution on the reagent zones should also be as short as possible. It is possible to select a centrifugal force which is so great that the solution is only braked by the capillary forces, i.e. the solution does not come to a standstill but rather passes through the corresponding reagent zones with the velocity brought about by the force ($Z_n - K_n$). If this procedure takes place in seconds or fractions of a second, then it can happen that higher reagent concentrations are obtained on the solution front, i.e. in the direction of the centrifugal force, a concentration increase builds up over the solution volume.

However, for the maintenance of definite reaction conditions, if necessary, an adjustment of uniform concentration relationships should take place. In order to remove such inhomogeneities, according to the present invention a so-called mixing valve (33) is provided. This mixing valve (33) has a closed boundary wall in the direction of the centrifugal force. At the bottom, there is arranged a surface-active chamber obliquely downwardly counter the direction of flow from the sample application chamber to the measurement point, for example arranged as a capillary, which bends round on its lower end and continues on to the reagent zone V. So long as the centrifugal force Z3 is greater than the capillary force in the bottom capillary K3, the fluid is kept firmly on the boundary wall. If Z3 is lowered to below the value of K3, then the capillary automatically sucks up fluid from the mixing chamber (33) into the associated capillary, previously existing gradients thereby being overcome and the capillary force transports the fluid to the reagent zone V. Therefore, expressed generally, the capillary force in the capillary of the mixing valve (33) here always acts as a transport force when $Z < K$.

The residence time in the mixing valve (33) is, in turn, freely selectable by the adjustment of the condition $Z_M > K_M$. The condition for the transport is thus precisely reversed to the above-described conditions.

The further steps over the reagent zones V to VII and to the mixing valve II (33a) do not need to be described again since they take place analogously to the previously described steps. In the described embodiment, the mixing valve (33a) is useful for transporting a homogeneous solution into the cuvette (34). In known embodiments of centrifugal analysers, the mixing is a laborious procedure since, for example, it is brought about by a strong acceleration and braking of the centrifuge or the flowthrough of the solution is accomplished with air. According to the present invention, this is avoided with technically simple means.

In the case of the second embodiment of the present invention, $K_2$ is a pressure force.

Figure 3:
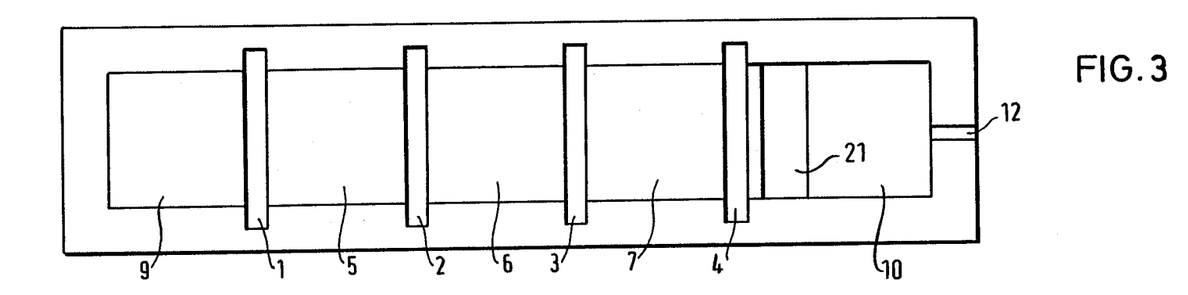
FIGS. 3, 4 and 5 illustrate views of another analysis element for the carrying out of the present invention.
Figure 4:
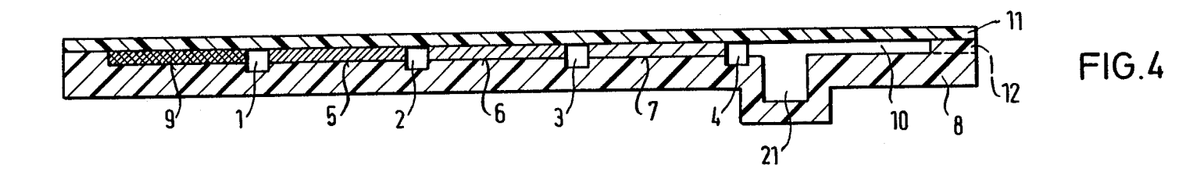
Figure 5:
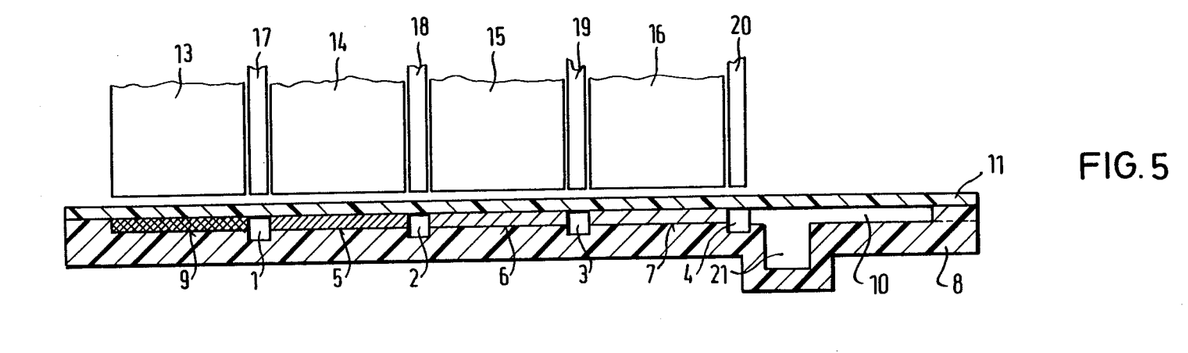

FIGS. 3, 4 and 5 of the accompanying drawings illustrate appropriate means for this embodiment in the form of disposable analysis elements.

In FIG. 3, such an element is schematically illustrated in plan view and in FIG. 4 in side view. The formed body (8), consisting of an appropriate material, for example a plastics material, has reagent carrier zones (5, 6, 7), which are placed in the plastics body. By means of an elastic closure fil (11), these reagent carrier zones are covered over. A sample application chamber (9) contains an absorbent inert compressable material which, for example, in a decompressed state, can take up 15 μl. of fluid and, in a compressed state, retains, for example, 2 μl. of fluid. A bulge in the body (8) serves as a measurement point or cuvette (21). Furthermore, the body (8) has an overflow chamber (10) and a ventilation bore (12).

Valve slots (1, 2, 3, 4) serve for the reception of valve plungers with which the individual reagent carrier zones can be separated from one another. Furthermore, plungers (13, 14, 15, 16) are provided, the base surfaces of which correspond exactly to the surface of the reagent carrier surface in question and serve the purpose of compressing the filled reagent zones (FIG. 5).

The course of the process in the case of this embodiment of the present invention is as follows:

A sample is introduced into the application chamber (9) by puncturing the foil (11) with a needle. Such an amount is injected that it completely fills the inert, absorbent fleece in the chamber (9) but does not give off any solution. Subsequently, for example by an appropriate control device, the plunger (13) is pressed on to the zone (9) so that the fluid is forced out of this zone and, by means of capillary force, is transported into zone (5). By means of the cohesion of the fluid, this is transferred practically completely to (5). Subsequently, valve plunger (17), for example also controlled by an appropriate mechanism, is pressed down so that (5) is separated from the application chamber (9). The foil (11) is adapted to the individual contours and serves as sealing membrane. The sample solution can be left to stand, i.e., incubate for a freely selectable time in the zone (5). However, as a rule, the dry reagent present in the zone (5) dissolves within a few seconds.

In the next step, plunger (14) presses on to the zone (5) so that the fluid is forced out of this zone and, due to the capillary suction action of the zone and, due to the capillary suction action of the zone (6), is transported into this. Thereafter, the valve plunger (18) is pressed down so that contact with the zone (5) is broken off. Here again, the time for dissolving the reagent in zone (6) can be freely chosen and, in general, again only takes a few seconds.

If, in the case of fluid transport due to capillary forces and in the case of the inflow into the reagent zone, a concentration gradient builds up, this can be overcome in that, before further transport to zone (7), a mixing step is introduced. By pressing down valve plunger (19), lifting up valve plunger (18) and plunger (14) and pressing down plunger (15), the fluid is transported back to zone (5). By lifting plunger (15) and pressing down plunger (14), the fluid is again pressed back to zone (6). It is possible to repeat this back-and-forth movement several times. Finally, the state is then again produced: plunger (14) pressed down, valve plunger (18) pressed down.

The further transport of the fluid from zone (6) to zone (7) takes place, possibly after lifting valve plunger (19), in an analogous manner by pressing down valve plunger (18) and pressing down plunger (15). The mixing procedure between zone (6) and zone (7) can, if desired, be repeated, analogously to the above-described manner, with the use of valve plunger (20).

After dissolving the reagent in zone (7), the thus resulting solution is then forced into the cuvette (21) by pressing down valve plunger (19) and pressing down plunger (15).

Thereafter, in an appropriate manner, the extinction change over a sufficiently long period of time is measured by any conventional process. From this signal change, again with conventional methods, there can be calculated the concentration of the substance to be analysed.

The means available for carrying out the change of the first or second force necessary for the process are, for the centrifugal force, in the first place changes of the speed of rotation and for the pressure force, the movement of the pressure plungers. The surface force can be regulated or changed not only by the shaping of the surface but also by the use of surface active agents. Preferred surface active agents are the polyoxiethylene derivatives. However, use can be made also of other nonionic, anionic, e.g. bile acids, or cationic surface active agents or mixtures thereof.

Examples of analyses which can be carried out according to the present invention are described in Federal Republic of Germany patent specification No. 30 40 385 (=U.S. patent application No. 323,205 filed Nov. 20, 1981). In particular, the process can be used for the determination of glucose, bilirubin, creatinine, albumin, protein, iron, haemoglobin, urea, uric acid, triglycerides, cholesterol, chloride, calcium, phosphate, γ-GT, alkaline phosphatase, GOT, GPT, lactate dehydrogenase, lipase, amylase, creatine kinase, thyroid hormones, acid phosphatase, drugs, cancer indicators and coagulation factors, in each case known reagents being used for these determinations.

The following Examples are given for the purpose of illustrating the present invention:

EXAMPLE 1

Glucose Determination with the use of an Insert Element According to FIGS. 1 And 2

On to filter papers of the size 6×6 mm. and with a thickness of 0.3 mm. there were applied the following reagents and then positioned in the described insert element as can be seen from FIG. 1:

| III | sodium phosphate buffer | 630 μg. |
| --- | --- | --- |
| | 2,4-dichlorophenolsulphonic acid | 466 μg |
| | Tween 20 (sorbinacrogol laurate) | 50 nl |
| | mannitol | 1 mg |
| IV | 4-aminoantipyrine | 24 μg. |
| VII | GOD (E.C. 1.1.3.4) | 2200 mU |
| | POD (E.C. 1.11.1.7) | 400 mU |

Human serum samples were diluted 1:200 with distilled water. 60 μl. of this diluted solution were introduced into the sample application chamber (1).

Centrifuging was carried out at 25° C. according to the following programme:

1. 10 sec. 180 r.p.m. moistening of the first fleece
2. 10 sec. 1500 r.p.m. centrifuging out into 1st mixing valve (3)
3. 15 sec. 0 r.p.m. transfer to V
4. 10 sec. 1500 r.p.m. centrifuging out into 2nd mixing valve (3a)
5. 15 sec. 0 r.p.m. emptying of the 2nd mixing valve (3a)
6. 10 sec. 150 r.p.m. transfer in the cuvette (4)
7. 5 sec. 1500 r.p.m. driving out of air bubbles
8. 225 sec. 360 r.p.m. measurement at 500 nm.

Figure 6:
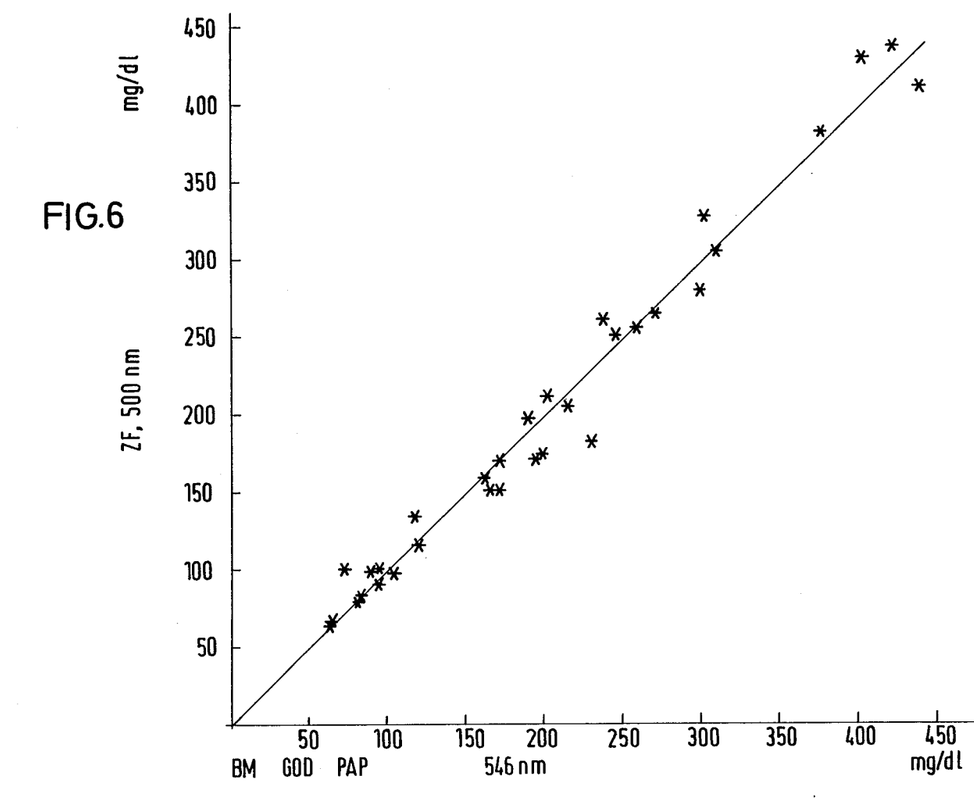
FIGS. 6, 7, 8, 9 and 10 show analysis results obtained according to the present invention, in graphic illustration.

The change of the extinction in dependence upon the time was measured and evaluated according to one of the conventional fixed time kinetic processes. The unknown concentration of glucose in the sample was determined after calibration of the process with a standard. The agreement with a comparative method, which was based on one of the known manual techniques, was very good, as can be seen from FIG. 6 which shows the results of the comparison method on the abscissae, the method according to the present invention on the ordinate.

On the ordinate, there are also plotted the values in the following Examples with the method according to the invention (symbol ZF).

EXAMPLE 2

Alkaline Phosphate Determination on the Insert Element According to FIGS. 1 And 2

On to filter paper of the size 6×6 mm. and with a thickness of 0.3 mm., there were applied the following reagents and then positioned as can be seen from FIG. 1:

| II | sodium carbonate buffer | 1200 μg. |
| --- | --- | --- |
| | magnesium aspartate | 16 μg. |
| III | sodium carbonate buffer | 1200 μg. |
| | magnesium aspartate | 16 μg. |
| VI | tris-p-nitrophenyl phosphate | 313 μg. |
| | tris | 31 μg. |

A human serum sample was diluted 1:10 with distilled water. 60 μl. of this dilute solution were introduced into the sample application chamber (1).

Centrifuging was carried out at 37° C. according to the following programme:

1. 10 sec. 180 r.p.m. moistening of the first fleece
2. 10 sec. 1500 r.p.m. centrifuging out into the 1st mixing valve (3)
3. 15 sec. 0 r.p.m. transfer to V
4. 10 sec. 1500 r.p.m. centrifuging out into the 2nd mixing valve (3a)
5. 15 sec. 0 r.p.m. emptying of the 2nd mixing valve (3a)
6. 10 sec. 150 r.p.m. transfer into the cuvette (4)
7. 5 sec. 1500 r.p.m. driving out of air bubbles
8. 225 sec. 360 r.p.m. measurement at 410 nm.

Figure 7:
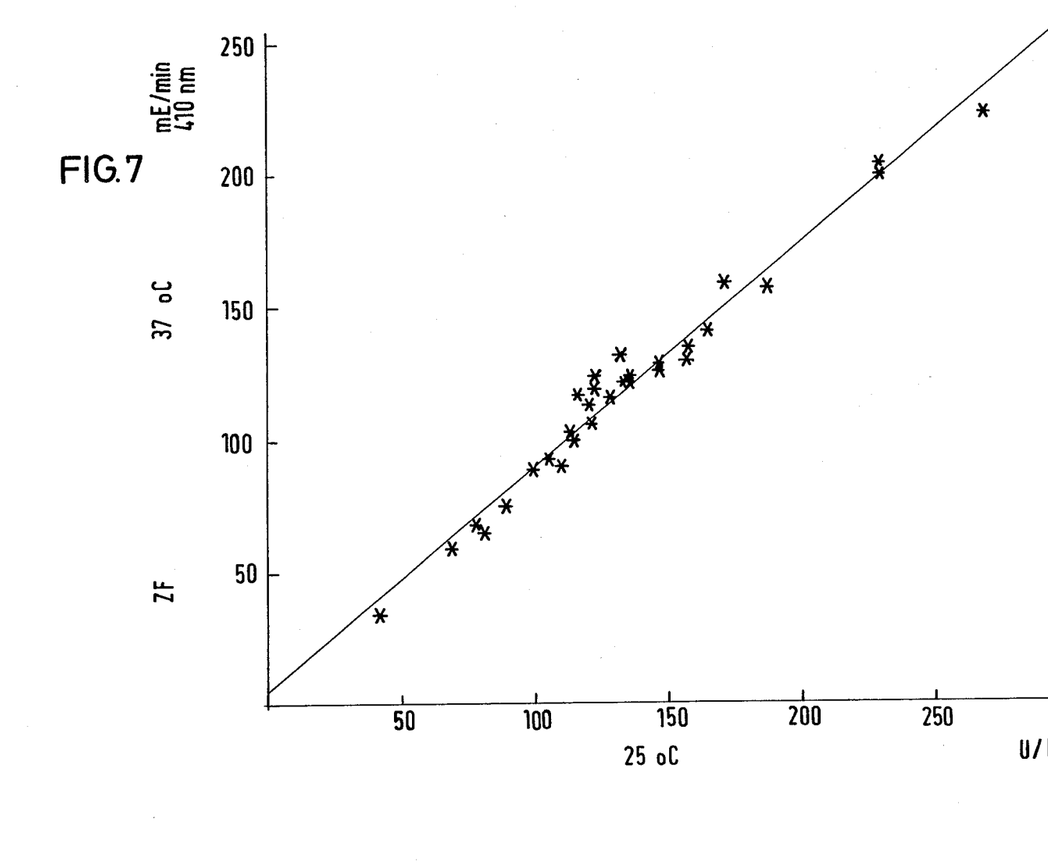

The monitored dependencies of the extinction on the time were evaluated according to one of the known processes in which the slope of the line is a measure of the activity of the enzyme to be determined. The unknown activities of alkaline phosphatase in the sample were determined after calibration of the process with a standard. The correlation with a comparative method, which was based on a known manual technique, was good, as can be seen from FIG. 7.

EXAMPLE 3

Bilirubin Determination with the Insert Element of FIGS. 1 and 2

On to filter papers of the size 6×6 mm. and with a thickness of 0.3 mm., there were applied the following reagents and positioned as can be seen from FIG. 1:

| II | 2,5-dichlorophenyldiazonium-naphthol-sulphonate | 68 μg. |
| --- | --- | --- |
| III | cetylpyridinium chloride | 1600 μg. |
| | tartaric acid | 2400 μg. |
| V | non-impregnated filter paper | |

Serum samples were diluted 1:10 with distilled wataer. 60 μl. of this dilute solution were introduced into the sample application chamber (1).

Centrifuging was carried out at 25° C. according to the following programme:

1. 10 sec. 180 r.p.m. moistening of the first fleece
2. 10 sec. 1500 r.p.m. centrifuging out into the 1st mixing valve (3)
3. 15 sec. 0 r.p.m. transfer to V
4. 10 sec. 1500 r.p.m. centrifuging out into the 2nd mixing valve (3a)
5. 15 sec. 0 r.p.m. emptying of the 2nd mixing valve (3a)
6. 10 sec. 150 r.p.m. transfer into the cuvette (4)
7. 5 sec. 1500 r.p.m. driving out of air bubbles
8. 225 sec. 360 r.p.m. measurement at 550 nm.

Figure 8:
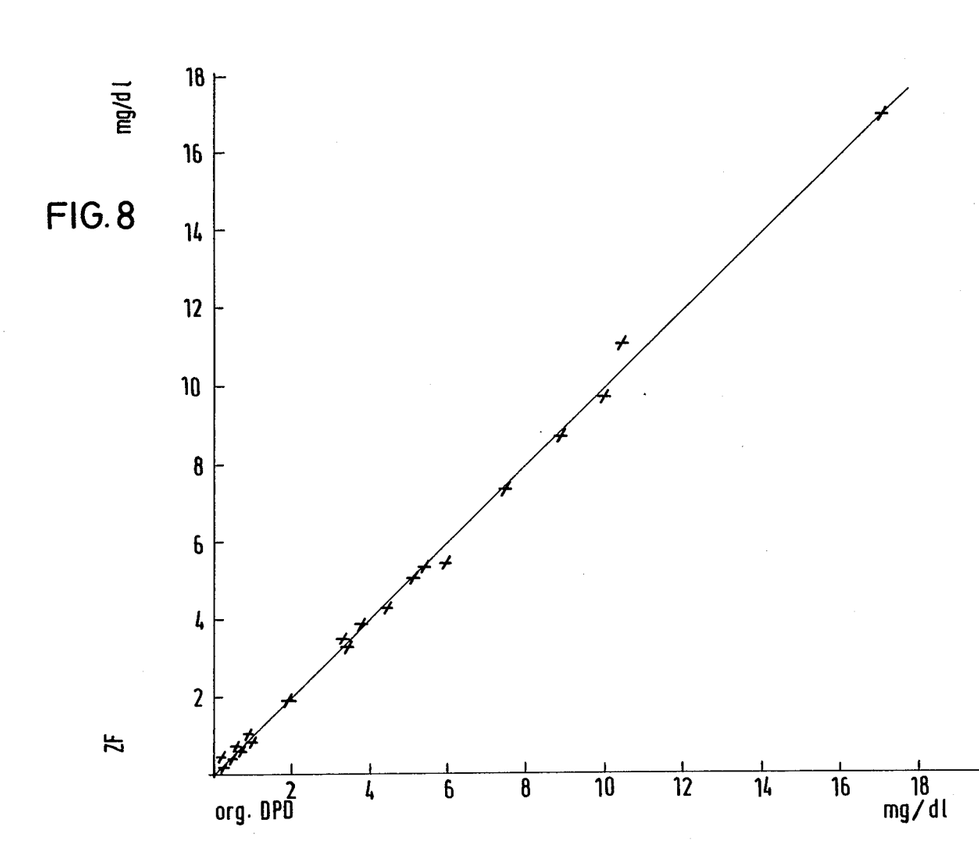

The monitored dependencies of the extinctions on the time were evaluated according to one of the usual end point processes; the unknown concentration s of bilirubin in the sample were determined after calibration of the process with a standard. The agreement with a comparison method, which was based on one of the known manual techniques, was very good, as FIG. 8 shows.

EXAMPLE 4

Creatine Kinase Determination with the Insert Element of FIGS. 1 and 2

On to filter papers of the size 6×6 mm. and with a thickness of 0.3 mm., there were applied the following reagents and positioned as can be seen from FIG. 1:

| IV | imidazole | 424 μg. |
| --- | --- | --- |
| | glucose | 240 μg. |
| | magnesium chloride hexahydrate | 128 μg. |
| | EDTA sodium salt | 47 μg. |
| | N—acetylcysteine | 205 μg. |
| | adenosine monophosphate sodium salt | 157 μg. |
| | adenosine diphosphate | 54 μg. |

|   | -continued | |
|---|---|---|
|   | diadenosine pentaphosphate lithium salt | 0.6 μg. |
|   | NADP sodium salt | 110 μg. |
| V | hexokinase (E.C. 2.7.1.1) | 218 mU |
|   | Glucose-6-phosphate-dehydrogenase (E.C.1.1.1.49) | 123 mU |
|   | creatine phosphate sodium salt | 615 μg. |

A human serum sample was diluted 1:25 with double distilled water. 60 μl. of this diluted solution were introduced into the sample application chamber (1).

Centrifuging was carried out at 37° C. according to the following programme:
1. 10 sec. 180 r.p.m. moistening of the first fleece
2. 10 sec. 1500 r.p.m. centrifuging out into the 1st mixing valve (3)
3. 15 sec. 0 r.p.m. transfer to V
4. 10 sec. 1500 r.p.m. centrifuging out into the 2nd mixing valve (3a)
5. 15 sec. 0 r.p.m. emptying of the 2nd mixing valve (3a)
6. 10 sec. 150 r.p.m. transfer into the cuvette (4)
7. 5 sec. 1500 r.p.m. driving out of air bubbles
8. 225 sec. 360 r.p.m. measurement at 340 nm.

Figure 9:
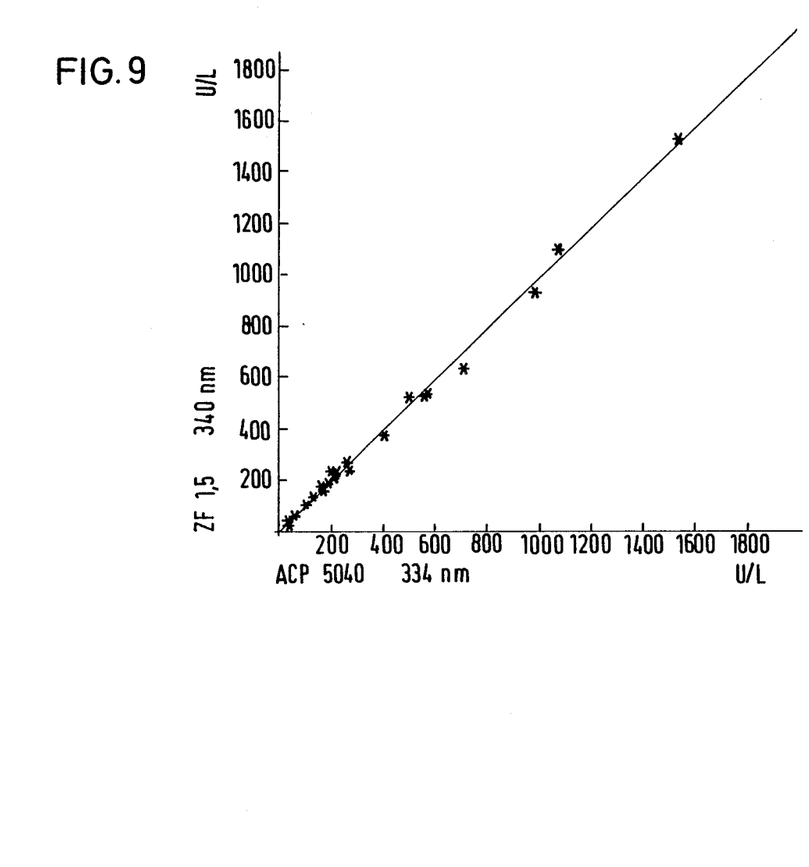

The monitored dependencies of the extinctions on the time were evaluated by one of the usual processes for kinetic measurements and the unknown activities of creatine kinase in the sample were determined after calibration of the process with a standard. The aggrement with a comparative method, which was based upon one of the known manual techniques, was very good, as shown in FIG. 9.

EXAMPLE 5

IgG Determination with the Insert Element of FIGS. 1 and 2

On to filter paper of the size 6×6 mm. and with a thickness of 0.33 mm., there were applied the following reagents and positioned as can be seen from FIG. 1 (in this case, two different reagent carrier papers were placed in the same chamber):

| V | sodium hydrogen phosphate dihydrate | 620 μg. |
|---|---|---|
|   | potassium dihydrogen phosphate | 107 μg. |
|   | polyethylene glycol 6000 | 1570 μg. |
| V | antibody against IgG (titre = 16 mg/ml) | 258 μg. |

A human serum sample was diluted 1:200 with distilled water. 60 μl. of this diluted solution were introduced into the sample application chamber (1).

Centrifuging was carried out at 25° C. according to the following programme:
1. 10 sec. 180 r.p.m. moistening of the first fleece
2. 10 sec. 1500 r.p.m. centrifuging out into the 1st mixing valve (3)
3. 15 sec. 0 r.p.m. transfer to V
4. 10 sec. 1500 r.p.m. centrifuging out into the 2nd mixing valve (3a)
5. 15 sec. 0 r.p.m. emptying of the 2nd mixing valve (3a)
6. 10 sec. 150 r.p.m. transfer into the cuvette (4)
7. 5 sec. 1500 r.p.m. driving out of air bubbles
8. 225 sec. 360 r.p.m. measurement at 340 nm.

Figure 10:
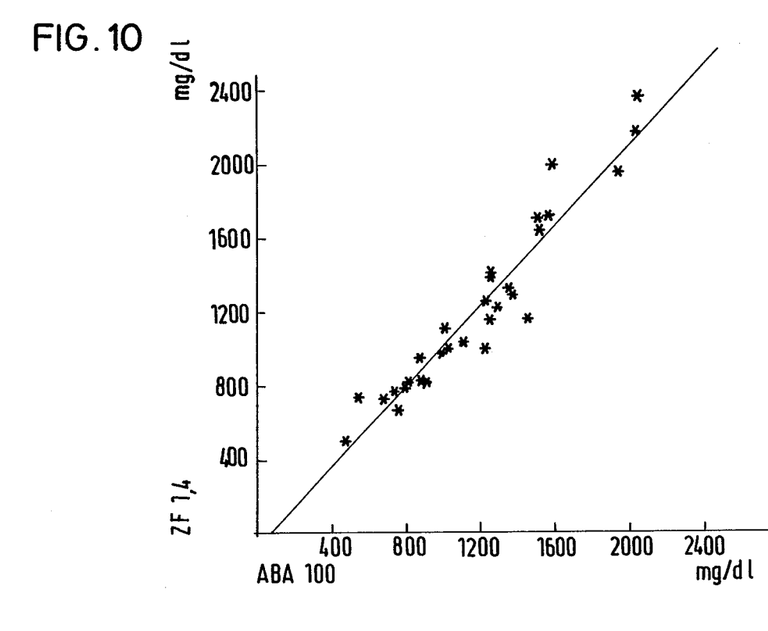

The monitored dependencies of the extinctions on the time were evaluated according to one of the usual processes for the evaluation of kinetic turbidity tests and the unknown concentrations of IgG in the sample were determined after calibration of the process with three standards of differing concentration and production of a calibration curve. The agreement with a comparative method, which was based on the automatic analyser "ABA 100" of the Firm Abbott, was very good, as FIG. 10 shows.

EXAMPLE 6

Glucose Determination with the Analysis Element According to FIG. 3

Reagent carrier papers of the size 6×6×0.3 mm. were prepared as follows: 10 82 1. of the reagent solutions, which contain a quarter of the amounts of substances used in the case of the different papers of Example 1, were applied to a paper of the given size.. The solutions were completely absorbed; subsequently, the solvent water was removed from the papers by lyophilisation.

The three different papers were placed in the three positions of the analysis element of FIG. 3 in the same sequence as in Example 1.

The sample was diluted 1:200 with double distilled water. 15 μl. of this diluted solution were introduced into the application chamber (9). The solution was then applied to the first reagent carrier (5) in the above-described manner. Residence time: 10 seconds. Subsequently, the solution was brought from (5) to (6), also in the manner already described. Residence time: 10 seconds. In analogous manner, the solution was brought to the reagent carrier 3 (7). Residence time: 5 seconds. From there, the solution was brought into the cuvette (21) by slowly depressing the plunger (16). The extinction was measured in it at 500 nm in known manner in dependence upon the time. From the course of this curve, with the known fixed time kinetic process, after calibration with a standard, the glucose concentration in unknown samples can be determined.

Aqueous solutions with the concentrations of 50, 100, 150, 200, 300 and 400 mg./di (adjusted by weighing) were investigated. The found amount was from 98 to 102%.

EXAMPLE 7

Alkaline Phosphatase Determination with the Element According to FIG. 3

Reagent carrier papers of the size 6×6×0.3 mm. were prepared as follows: 10 μl. of the reagent solutions, which contained precisely one quarter of the amounts of substances contained in the various papers of Example 2, were applied to a paper of the given size. The solutions were completely absorbed; subsequently, the solvent water was removed from the papers by lyophilisation.

The two papers were placed in the first two positions of the analysis element of FIG. 3 in the same sequence. A paper which did not contain reagent was placed in the third position.

The sample was diluted 1:10 with distilled water. 15 μl. of this diluted solution was introduced into the application chamber (9). The solution was then brought on to the first reagent carrier (5) in the described manner. Residence time: 10 seconds. Subsequently, the solution was brought from (5) to (6), again in the already described manner. Residence time: 10 seconds. In analogous manner, this solution was brought on to the empty fleece (7). Residence time: 5 seconds. From there, the solution was brought into the cuvette (21) by slowly lowering the plunger (16). The extinction was followed in the cuvette at 410 nm in dependence upon the time. From the course of the plotted line, with known kinetic determination processes, after calibration with a standard, there can be determined the activity of the alkaline phosphatase in unknown samples.

Various control sera were investigated, which contained activities of between 30 and 600 U/liter. The found amount was from 90 to 110%.

EXAMPLE 8

Creatine Kinase Determination with the Element According to FIG. 3

Reagent carrier papers of the size 6×5×0.3 mm. were prepared as follows: 10 μl. of the reagent solutions, which contained precisely one quarter of the amounts of substances contained in the various papers of Example 4, were applied to a paper of the given size. The solutions were completely absorbed; subsequently, the solvent water was removed from the papers by lyophilisation.

The two papers were placed in the same sequence as in Example 4 in the first two positions of the analysis element of FIG. 3. A paper of the same kind, which contained no reagent, was placed in the third position.

The sample was diluted 1:25 with double distilled water, 15 μl. of this diluted solution were introduced into the application chamber (9). The solution was then brought on to the first reagent carrier (5) in the described manner. Residence time: 10 seconds. Subsequently, the solution was brought from (5) to (6) in the also already described manner. Residence time: 10 seconds. In analogous manner, the solution was moved to the zone (7). Residence time: 5 seconds. From there, the solution was brought into the cuvette (21) by slowly lowering the plunger (16). In it, in known manner, the extinction is followed at 340 nm in dependence upon the time. After a curved initial phase, a linear course of this function was obtained. From this part, with the help of known evaluation processes for kinetic methods, after calibration with a standard, there was determined the activity of creatine kinase in an unknown sample.

Various human serum samples were enriched with purified enzyme in such a manner that they contained activities of from 5 to 800 U/liter. Comparative values were obtained by a manual measurement. The amounts found, in comparison with these manual values, were from 92 to 110%.

It will be understood that the specification and examples are illustrative but not limitative of the present invention and that other embodiments within the spirit and scope of the invention will suggest themselves to those skilled in the art.

What is claimed is:

1. Process for analyzing a liquid sample, comprising:
   (a) transporting a fluid sample from a sample application point to a soluble dry reagent containing zone on a transport path;
   (b) mixing and incubating said fluid sample with said dry reagent to form a reaction-mixture; and
   (c) transporting said reaction mixture to a reaction-mixture measurement point on said transport path at which point a parameter of said reaction mixture is measured, wherein transport of said fluid sample and said reaction mixture takes place on at least a part of said transport path by interaction of a first, surface force between said fluid sample or said reaction-mixture and said transport path and a second, controllably variable centrifugal force, said second controllably variable centrifugal force being less than said surface force on said at least part of said transport path so as to cause said fluid sample or reaction-mixture to move in a direction opposite the direction of said controllably variable centrifugal force during transport of the fluid sample from the application point to the dry reagent zone and the reaction mixture from the dry reagent zone to the point of measurement.

2. Process of claim 1, wherein transporting said sample comprises:
   (a) dimensioning a portion of the transport path for transporting said sample and said reaction mixture at the reagent containing zone, said dimensioning providing the surface force on the sample, and
   (b) controllably rotating said transport path to produce a controllably variable centrifugal force, which centrifugal force has a component along the transport path.

3. Process according to claim 1, comprising controllably rotating said transport path by controlling a centrifugal rotor on which said path is placed.

4. Process of claim 1 wherein said dimensioning comprises providing an absorbent carrier in the zone.

5. Process of claim 4, wherein said absorbent carrier contains a dry reagent.

* * * * *